(12) United States Patent  (10) Patent No.: US 9,024,263 B2
Tonami                      (45) Date of Patent:      May 5, 2015

(54) RADIATION TOMOGRAPHY APPARATUS FOR SMALL ANIMALS

(75) Inventor: Hiromichi Tonami, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 258 days.

(21) Appl. No.: 13/297,215

(22) Filed: Nov. 15, 2011

(65) Prior Publication Data

US 2012/0145909 A1    Jun. 14, 2012

(30) Foreign Application Priority Data

Dec. 9, 2010   (JP) .................... 2010-274577

(51) Int. Cl.
  *A61B 6/00*   (2006.01)
  *A61B 6/03*   (2006.01)
  *A61B 6/04*   (2006.01)

(52) U.S. Cl.
  CPC ............. *A61B 6/032* (2013.01); *A61B 6/037* (2013.01); *A61B 6/0421* (2013.01); *A61B 6/0442* (2013.01); *A61B 6/4417* (2013.01); *A61B 6/508* (2013.01)

(58) Field of Classification Search
  CPC .................................................. A61B 6/0421
  USPC .......... 250/363.02–363.04, 363.09; 378/4, 13
  See application file for complete search history.

(56) References Cited

U.S. PATENT DOCUMENTS

| | | | |
|---|---|---|---|
| 6,987,270 B2 * | 1/2006 | Trotter | 250/395 |
| 7,352,840 B1 * | 4/2008 | Nagarkar et al. | 378/19 |
| 7,723,691 B2 | 5/2010 | Tonami | |
| 8,294,108 B2 * | 10/2012 | Tonami et al. | 250/363.02 |
| 2004/0195512 A1 * | 10/2004 | Crosetto | 250/363.04 |
| 2012/0321033 A1 * | 12/2012 | Stearns et al. | 378/4 |
| 2013/0156150 A1 * | 6/2013 | Tonami | 378/9 |

FOREIGN PATENT DOCUMENTS

| | | |
|---|---|---|
| JP | 2005-140560 A | 6/2005 |
| WO | WO-2007/141831 A1 | 12/2007 |

OTHER PUBLICATIONS

Cheng et al., "A Rat Head Holder for Simultaneous Scanning of Two Rats in Small Animal PET Scanners: Design, Construction, Feasibility Testing and Kinetic Validation," Journal of Neuroscience Methods 176 (2009): p. 24-33.*

Dazai et al., "Multiple Mouse Biological Loading and Monitoring System for MRI," Magnetic Resonance in Medicine 52:709-715 (2004): p. 709-715.*

Habte et al. "Impact of a Multiple Mice Holder on Quantitation of High-Throughput MicroPET Imaging With and Without CT Attenuation Correction," Mol Imaging Biol (2013) 15: p. 569-575.*

(Continued)

*Primary Examiner* — Casey Bryant

(74) *Attorney, Agent, or Firm* — Cheng Law Group, PLLC

(57) ABSTRACT

Disclosed is radiation tomography apparatus for smaller animals including a radiation source for emitting radiation; a radiation detecting device for detecting radiation; a rotary device for rotating the radiation source; and a holder provided between the radiation source and the radiation detecting device that has two or more spaces for placing a subject. The holder includes space discriminating members for each of the spaces. Each of the space discriminating members has a unique sectional shape when cut along a plane where an imaginary circle exists. Here, the imaginary circle is a locus of rotation of the radiation source.

16 Claims, 6 Drawing Sheets

(56) References Cited

OTHER PUBLICATIONS

Siepel et al. "Scanning multiple mice in a small-animal PET scanner: Influence on image quality," Nuclear Instruments and Methods in Physics Research A 621 (2010): p. 605-610.*

Notification of Reasons for Refusal for the Application No. 2010-274577 from Japan Patent Office mailed Jan. 21, 2014.

* cited by examiner

RADIATION TOMOGRAPHY APPARATUS FOR SMALL ANIMALS

BACKGROUND OF THE INVENTION (1) Field of the Invention

This invention relates to radiation tomography apparatus for smaller animals for taking a tomography image of a smaller animal as a research subject. More particularly, this invention relates to radiation tomography apparatus for smaller animals for imaging two or more small animals at one time.

(2) Description of the Related Art

One example of apparatus for imaging a smaller animal as a research subject includes radiation tomography apparatus for smaller animals. This apparatus allows generation of a tomography image of a smaller animal. An experimenter can recognize an internal structure of the small animal referring to the image. See, for example, Patent Literature 1.

Description will be given of a conventional configuration of such radiation tomography apparatus for smaller animals. As shown in FIG. 10, the conventional apparatus includes a gantry 51 having an opening. The gantry 51 includes inside thereof a radiation source 53 for emitting radiation and a radiation detector 54 for detecting radiation. The radiation source 53 and the radiation detector 54 are placed as to interpose the opening of the gantry 51, and allow rotation about the opening with a relative position thereof being maintained. A smaller animal as a subject is placed inside the opening.

Description will be given of operations of the conventional radiation tomography apparatus for smaller animals. For acquiring a tomography image of a subject with use of the conventional apparatus, the subject is firstly inserted into the opening of the gantry 51. Then, imaging is performed two or more times while the radiation source 53 and the radiation detector 54 rotate about the subject. The acquired fluoroscopic images each contain images of the subject taken in different directions. These fluoroscopic images are constructed, whereby a tomography image of the subject is to be generated.

The results obtained typically have some variations due to individual differences and errors in measurement of smaller animals in physiological experiments. Accordingly, in the experiments with smaller animals, similar experiments are conducted to two or more smaller animals for obtaining experimental results in consideration of result variations. Thus, imaging with the radiation tomography apparatus for smaller animals is usually conducted for two or more smaller animals. In other words, one experiment is conducted through repeated imaging for every smaller animal.

Here, tomography apparatus has been invented that allows imaging of two or more smaller animals at one time. This will improve efficiency in experimental procedures.

[Patent Literature 1] WO 2007/141831

The conventional configuration, however, has the following problem. That is, the conventional configuration may obtain only a tomography image having difficulties with diagnosis. With the conventional apparatus, an image is to be obtained having sectional images of two or more smaller animals contained in a filed of view thereof. The sectional images of smaller animals contained in the image are similar to one another. Thus, it is difficult to determine correspondence between a sectional image and the subject individually.

As above, in the conventional tomography apparatus, an experimenter has to study a portion in the tomography image individually where each image of the smaller animals used in the experiment is contained at every generation of the tomography image. When an experimenter mistakes a subject during such operation and diagnoses a tomography image of the mistaken subject, a result different from an actual phenomenon may possibly be obtained. Accordingly, a design is needed for clearly distinguishing two or more sectional images of the smaller animal contained in the tomography image.

SUMMARY OF THE INVENTION

This invention has been made regarding the state of the art noted above, and its object is to provide radiation tomography apparatus for smaller animals that allows imaging of two or more subjects at one time while distinguishing the subjects individually This invention is constituted as stated below to achieve the above object. That is, this invention discloses radiation tomography apparatus for smaller animals including a radiation source for emitting radiation; a radiation detecting device for detecting radiation; a rotary device for rotating the radiation source; and a holder provided between the radiation source and the radiation detecting device that has two or more spaces for placing a subject. The holder includes space discriminating members for each of the spaces. Each of the space discriminating members has a unique sectional shape when cut along a plane where an imaginary circle exists. Here, the imaginary circle is a locus of rotation of the radiation source.

According to this invention, radiation tomography apparatus for smaller animals may be provided that allows accurate discrimination of the subjects in imaging two or more subjects at one time. Specifically, each space for holding the subject in the holder for holding two or more subjects includes the space discriminating member having a unique sectional shape for space discrimination. The apparatus according to this invention generates a tomography image having a sectional image of the space discriminating member contained therein. Here, taking into consideration that the space discriminating member has the sectional shape that may be used for space discrimination, a graphic symbol that discriminates each space for holding the subject is contained in the image naturally upon imaging a tomography image of the subject. Consequently, an experimenter may discriminate each sectional image of the subject contained in the tomography image differentially without mistaking the images.

Moreover, in the foregoing radiation tomography apparatus for smaller animals, the space discriminating member is inserted inside of the space. Such configuration is more desirable.

The foregoing configuration is one example of specific aspects of this invention. The space discriminating member is inserted inside of the space, whereby a tomography image may be taken with the space accurately associated with the space discriminating member.

Moreover, in the foregoing radiation tomography apparatus for smaller animals, one subject is inserted into each of the spaces provided in the holder. Such configuration is more desirable.

The foregoing configuration is one example of specific aspects of this invention. When one subject is inserted into each of the spaces, the subject may be imaged while being isolated individually. Accordingly, acquisition of an image may be prevented having difficulty with diagnosis due to an unclear boundary between the subjects overlapping one another.

Moreover, the space discriminating member of the foregoing radiation tomography apparatus for smaller animals is made from an acrylic resin. Such configuration is more desirable.

The foregoing configuration is one example of specific aspects of this invention. The holder made from a radio-transparent acrylic resin may prevent the space discriminating member from absorbing excessive doses of radiation to affect the tomography image of the subject. Consequently, the radiation tomography apparatus for smaller animals may be provided that allows acquisition of a clearer tomography image.

Moreover, the foregoing radiation tomography apparatus for smaller animals includes a top board for supporting the holder, and a top board moving device for moving the top board in a direction perpendicular to the imaginary circle. Such configuration is more desirable.

The foregoing configuration is one example of specific aspects of this invention. Here, the holder includes the top board that allows support and free slide. Consequently, the radiation tomography apparatus for smaller animals may be provided that allows easy guidance of the subject into the field of view.

Moreover, the foregoing radiation tomography apparatus for smaller animals further includes positron emission type tomography apparatus adjacent to the radiation source and the radiation detecting device in a direction perpendicular to the imaginary circle. Such configuration is more desirable.

The foregoing configuration is one example of specific aspects of this invention. With the positron emission type tomography apparatus, functional and structural images may both be acquired, which results in more information acquired through imaging.

According to this invention, radiation tomography apparatus for smaller animals may be provided that allows accurate discrimination of the subjects in imaging two or more subjects at one time. Specifically, each space for holding the subject in the holder for holding two or more subjects includes the space discriminating member having a unique sectional shape for space discrimination. A graphic symbol that discriminates each space for holding the subject is contained in the image naturally upon imaging a tomography image of the subject. Consequently, an experimenter may discriminate each sectional image of the subject contained in the tomography image differentially without mistaking the images.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DESCRIPTION OF THE PREFERRED EMBODIMENTS

Figure 1:
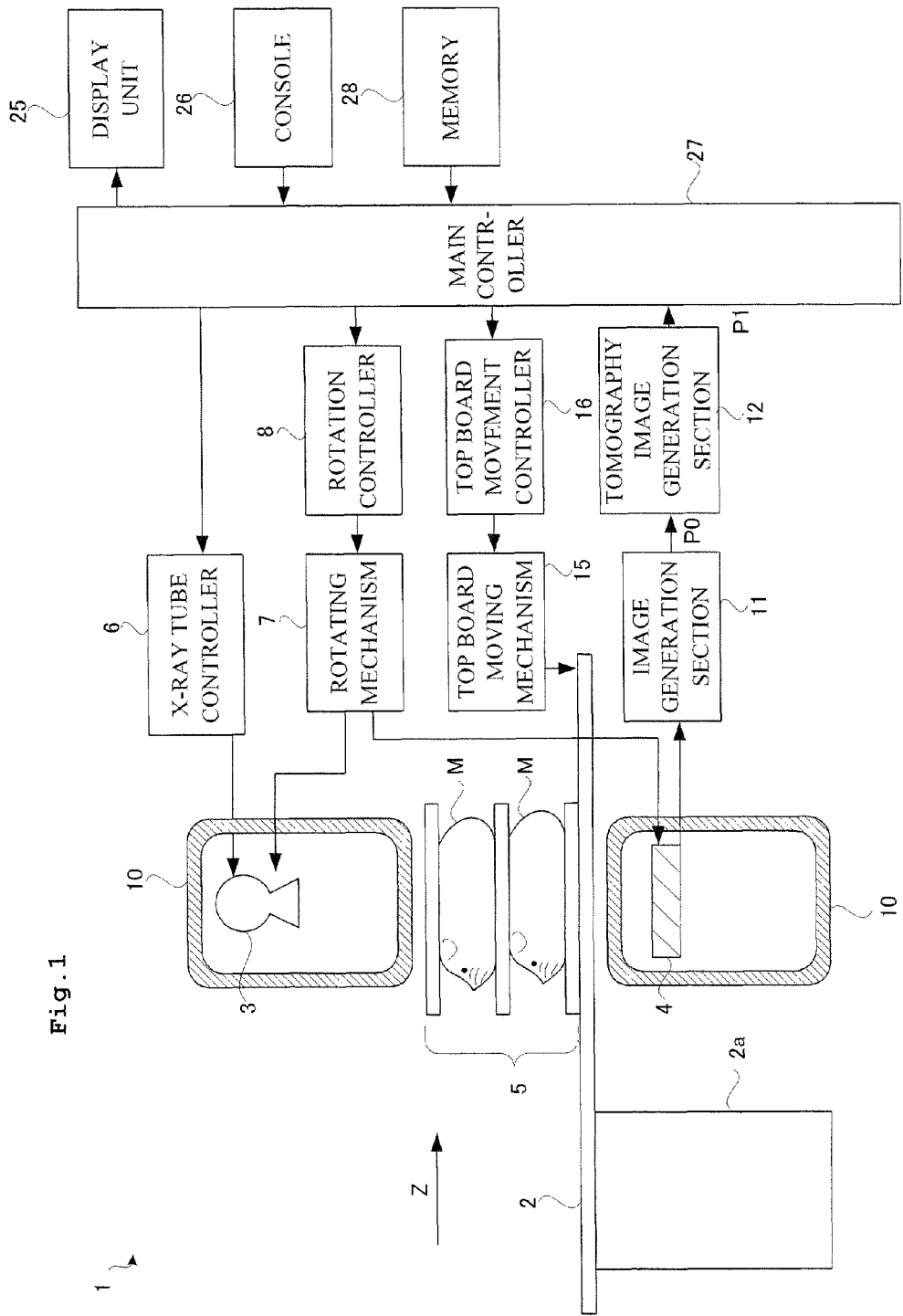
FIG. 1 is a functional block diagram illustrating a configuration of X-ray tomography apparatus according to Embodiment 1.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

Embodiments of this invention will be described hereinafter. X-rays in the embodiments correspond to radiation in this invention. An FPD is the abbreviation of a flat panel detector. Moreover, X-ray tomography apparatus of this invention is for smaller animals, such as a mouse.

Firstly, description will be given of a configuration of X-ray tomography apparatus according to Embodiment 1. As shown in FIG. 1, the X-ray tomography apparatus 1 includes a top board 2 for supporting a subject M, and a gantry 10 with a through hole passing in a direction where the top board 2 extends. The top board 2 is inserted into the through hole of the gantry 10. The top board 2 freely moves in and out along a direction where the top board 2 extends relative to a support table 2a for supporting the top board 2 (hereinafter, a perpendicular direction to an imaginary circle VC.) The top board 2 is moved by a top board moving mechanism 15. The top board moving mechanism 15 is controlled by a top board movement controller 16. The top board moving mechanism 15 corresponds to the top board movement controller in this invention.

The gantry 10 includes inside thereof an X-ray tube 3 for emitting X-rays, and an FPD 4 for detecting X-rays. X-rays from the X-ray tube 3 pass across the through hole of the gantry to reach the FPD 4. The X-ray tube 3 corresponds to the radiation source in this invention. The FPD 4 corresponds to the radiation detecting device in this invention.

An X-ray tube controller 6 controls the X-ray tube 3 with a given tube current, a tube voltage, and a pulse width. The FPD 4 detects X-rays emitted from the X-ray tube 3 and transmitting through the subject M, and generates detection signals. The detection signal is sent out to an image generation section 11, where a fluoroscopic image P0 is generated having a projected image of the subject M contained therein. A tomography image generation section 12 generates a tomography image P1 based on the fluoroscopic image P0 generated in the image generation section 11 through cutting the subject M along any sectional plane.

Figure 2:
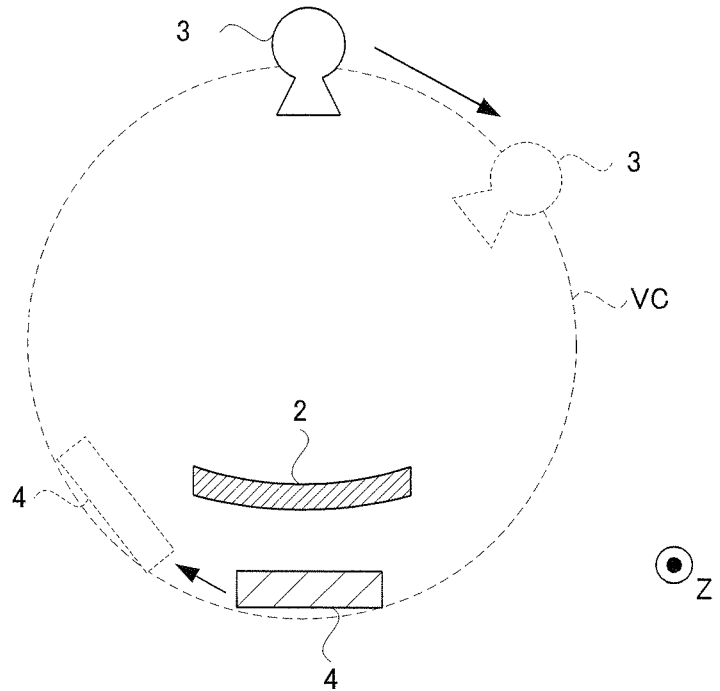
FIG. 2 is a schematic view illustrating rotation movement of an X-ray tube and an FPD according to Embodiment 1.

Description will be given of rotation of the X-ray tube 3 and the FPD 4. The X-ray tube 3 and the FPD 4 rotate integrally with a rotating mechanism 7 about a central axis in a direction where the top board 2 extends. Specifically, as shown in FIG. 2, the X-ray tube 3 and the FPD 4 move and rotate while a relative positional relationship therebetween is maintained. Herein, the rotating mechanism 7 rotates the X-ray tube 3 along an imaginary circle VC having a center as a midpoint on a line connecting the X-ray tube 3 and the FPD 4. A direction perpendicular to the imaginary circle VC (i.e., a direction passing through the plane of FIG. 2: z-direction) corresponds to the direction where the top board 2 extends. A rotation controller 8 is provided for controlling the rotating mechanism 7. The rotating mechanism 7 corresponds to the rotating device in this invention.

Figure 3:
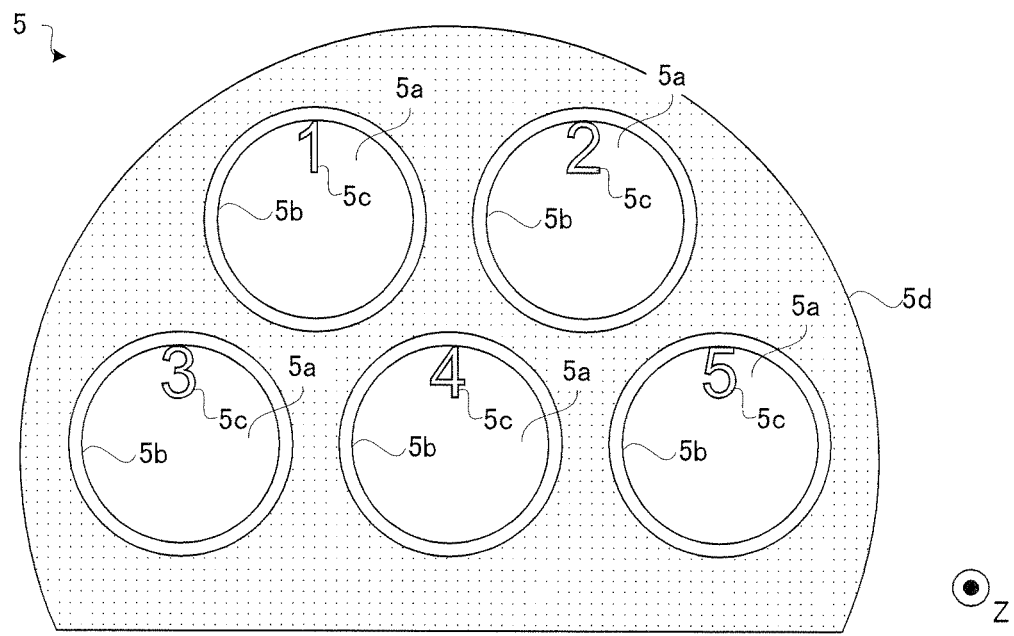
FIG. 3 is a plan view illustrating a holder according to Embodiment 1.

The top board 2 has the holder 5 placed thereon for holding the subject M. Description will be given of a configuration of the holder 5. As shown in FIG. 3, the holder 5 includes five spaces 5a in a circular shape, the circular being cylindrical extending in the z-direction when considered as a solid. Each one subject M is inserted into every space 5a. A cylinder 5b forms an inner wall of the space 5a. The cylinder 5b is embedded in each through hole for support in a Styrofoam cylindrical support member 5d having two or more holes opened in a lotus shape in the z-direction. Moreover, the cylinder 5b is composed of an acrylic resin easy to transmit X-rays. The holder 5 has three spaces 5a on a first step on a near side to the top board 2, and two spaces 5a on a second step on a far side from the top board 2.

As shown in FIG. 3, a columnar space discriminating member 5c is attached to each of the spaces 5a in the holder 5. When seen in the z-direction, the space discriminating member 5c is in an Arabic numeral shape, and is each inserted inside of every space 5a. Taking into consideration that one subject M is inserted into the space 5a, one space discriminating member 5c is provided for one subject.

Moreover, as shown in FIG. 3, the space discriminating members 5c provided in the spaces 5a of the holder 5 differ from one another in shape when seen in the z-direction. That is, the shape of the space discriminating member 5c is each in an Arabic numeral shape of 1 to 5. Moreover, the space discriminating members 5c are placed such that the spaces 5a of the holder 5 are numbered from an upper left side.

Figure 4:
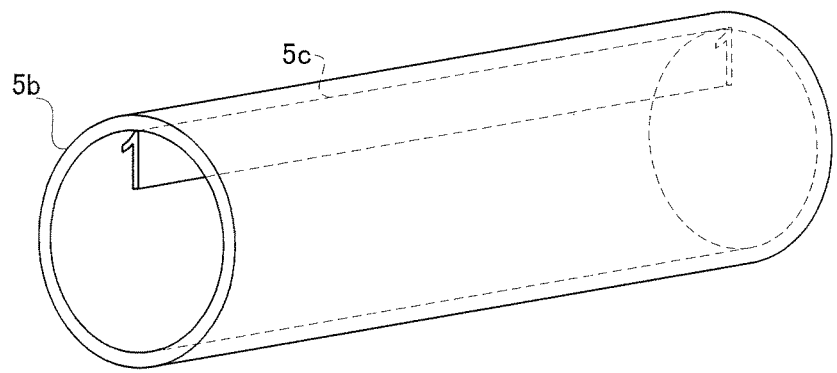
FIG. 4 is a perspective view illustrating the holder according to Embodiment 1.

FIG. 4 is a perspective view showing one of the cylinders 5b that forms the inner wall of the space 5a. As shown in FIG. 4, the space discriminating member 5c is provided on an upper portion of the inner wall of the cylinder 5b. Accordingly, the space discriminating member 5c is not obstructive when the subject M is inserted inside of the cylinder 5b.

When cut along a plane where the imaginary circle VC exists, the space discriminating members 5c each have a sectional shape of Arabic numeral numbers of 1 to 5, which is similar to that seen the space discriminating member 5c in the z-direction. Moreover, when the space discriminating member 5c is cut along a plane parallel to the foregoing plane, the space discriminating members 5c also each have a sectional shape of Arabic numeral numbers of 1 to 5. As above, the sectional image appearing upon cutting of the space discriminating member 5c along the plane where the imaginary circle VC exists verifies the space 5a (i.e., the subject). In other words, each of the space discriminating members 5c has a unique sectional shape when cut along a plane parallel to the imaginary circle VC.

A display unit 25 is provided for displaying a tomography image P1 acquired through radiography. A console 26 is provided for inputting experimenter's instructions such as start of emitting X-rays. A main controller 27 is also provided for controlling each controller en bloc. The main controller 27 has a CPU, and realizes each controller 6, 8, 16 and each section 11, 12 by executing various programs. The above components may be divided into arithmetic units that perform their functions. A memory unit 28 memorizes all parameters with respect to control of the X-ray tomography apparatus 1 such as a parameter used for imaging and an intermediate image generated in connection with image processing.

<Operation of X-Ray Tomography Apparatus>

Figure 5:
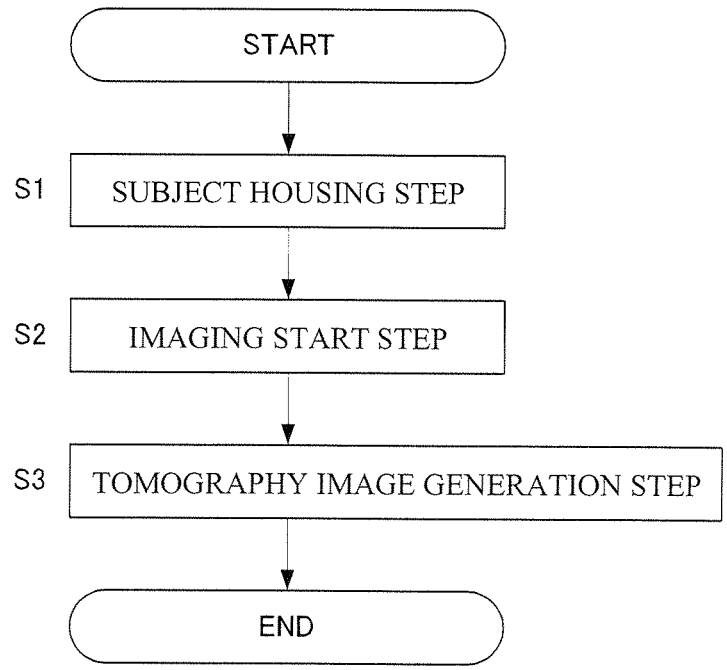
FIG. 5 is a flow chart illustrating operation of the X-ray tomography apparatus according to Embodiment 1.

Next, description will be given of operations of the X-ray tomography apparatus 1. As shown in FIG. 5, for acquiring a tomography image P1 for smaller animals with use of the X-ray tomography apparatus 1 according to Embodiment 1, firstly a subject M is housed into the holder 5 (Subject Housing Step S1.) Thereafter, imaging of a fluoroscopic image P0 is started (Imaging Start Step S2.) Then, a tomography image P1 is generated (Tomography Image Generation Step S3.) Each of these steps will be described hereinafter in order.

<Subject Housing Step S1>

Prior to radiography, the subjects M are under anesthesia so as not to move during radiography. Each of the anesthetized subjects M is housed into the space 5a of the holder 5. Herein, one subject M is housed per space 5a of the holder 5. Since the holder 5 is provided with five spaces 5a, five subjects M may be housed in the holder 5. The holder 5 having a plurality of subjects M housed therein is placed on the top board 2.

<Imaging Start Step S2>

When the experimenter provides instructions via the console 26 to the X-ray tomography apparatus 1 to start radiography, the top board 2 slides to guide the subject M into the through hole of the gantry 10 (see FIG. 1.) An X-ray tube controller 6 emits X-rays intermittently in accordance with an irradiation time, a tube current, and a tube voltage stored in the memory 28. Meanwhile, the rotating mechanism 7 rotates the X-ray tube 3 and the FPD 4. The FPD 4 detects X-rays from the X-ray tube 3 that transmits through the subject M, and sends detection data at this time to the image generation section 11.

The image generation section 11 images detection data sent out from the FPD 4, and generates the fluoroscopic imaging P0 having intensity of X-rays being mapped therein. The FPD 4 sends out data to the image generation section 11 in every emission of X-rays from the X-ray tube 3. Accordingly, the image generation section 11 generates a plurality of the fluoroscopic images P0. The fluoroscopic images P0 are acquired while the X-ray tube 3 and the FPD 4 move and rotate. Consequently, the fluoroscopic images P0 each contain fluoroscopic images of the subject M in various perspective directions. The X-ray tube 3 completes emission of X-rays upon one complete rotation of the X-ray tube 3 and the FPD 4 from starting of radiography.

Figure 6:
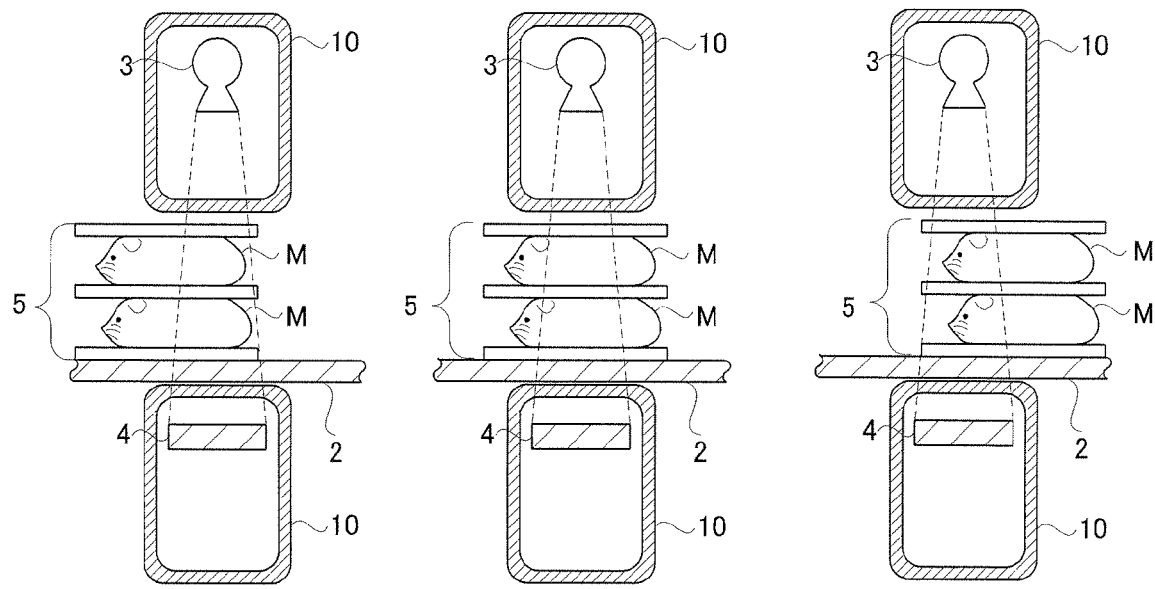
FIG. 6 is a sectional view illustrating operation of the X-ray tomography apparatus according to Embodiment 1.

Description will be given of movement of the top board 2 after starting of radiography. The X-ray tomography apparatus 1 images only a part of the subject M at one time. That is because the filed of view in the X-ray tomography apparatus 1 has a width smaller than the subject M in the z-direction. Accordingly, with Embodiment 1, imaging by one complete rotation of the X-ray 3 and the FPD 4 as above is to be conducted two or more times, whereby a tomography image may be obtained for the entire subject M. Specifically, as shown on the left of FIG. 6, a tail of the subject M is firstly imaged. Thereafter, the top board 2 slides to vary a relative position between the subject M and the gantry 10. Then, as shown in the middle of FIG. 6, an abdomen of the subject M is imaged. Thereafter, the top board 2 slides again, and a head of the subject M is imaged as shown on the right of FIG. 6. In such way, fluoroscopic images P0 is acquired for the entire subject.

<Tomography Image Generation Step S3>

The fluoroscopic imaging P0 is sent to the tomography image generation section 12. The tomography image generation section 12 reconstructs a series of fluoroscopic images P0 having information on three-dimensional configuration through imaging in various directions, thereby generating the tomography images P1 in which the subject M with a body axis in the z-direction is cut into round slices. The position cut into round slices varies in the z-direction, whereby two or more tomography images P1 are generated. The tomography image P1 generated in such way is displayed on the display unit 25, and radiography is completed. That is, the tomography images P1 are cross section images when the subject M is cut along a plane where the imaginary circle VC exists, and a plane parallel to this.

Figure 7:
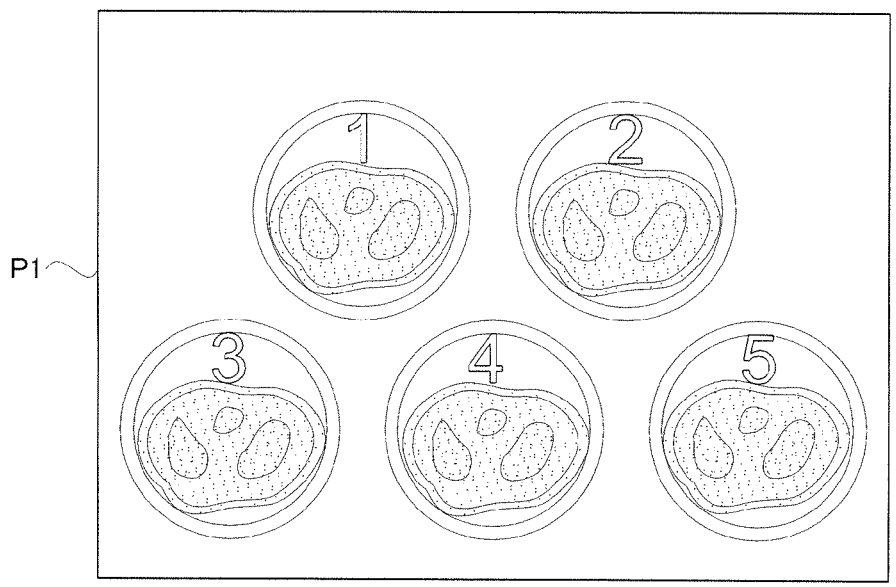
FIG. 7 is a sectional view illustrating a tomography image according to Embodiment 1.

The tomography image P1 acquired at this time will be further described. As shown in FIG. 7, the tomography image P1 includes a cross section of the space discriminating member 5c along with the cross section image of the subject M. When cut along a plane parallel to the plane where the imaginary circle VC exists, the space discriminating member 5c has a cross section in an Arabic numeral shape. Accordingly, an image of the space discriminating member 5 is contained in the tomography image P1 in an Arabic numeral shape. The experimenter may discriminate the subject M individually based on the Arabic numerals appearing in the tomography image P1.

As above, according to Embodiment 1, the X-ray tomography apparatus 1 may be provided that allows accurate discrimination of the subject M in once imaging of two or more subjects M at one time. Specifically, the space discriminating member 5c having a cross section for space discrimination is provided for each of the spaces 5a in the holder 5 for supporting two or more subjects. The cross section of the space discriminating member 5c is contained in the tomography image P1 generated with the apparatus according to Embodiment 1. Taking into consideration that the cross sectional shape of the space discriminating member 5c is usable for discriminating the space 5a, the graphic symbol that verifies each of the spaces 5a for supporting the subject is naturally contained upon imaging the cross section of the subject M. Accordingly, the experimenter may recognize each cross section of the subject M contained in the tomography image P1 with no mistake.

Moreover, when one subject M is inserted into each of the spaces 5a, the subject M may be imaged while being isolated individually. Accordingly, acquisition of an image may be prevented having difficulty with diagnosis due to an unclear boundary between the subjects overlapping one another.

Moreover, the holder 5 made from an acrylic resin that is transparent to X-rays may prevent the space discriminating member 5c from absorbing excessive doses of X-rays to affect the tomography image of the subject M. Consequently, the X-ray tomography apparatus 1 for smaller animals may be provided that allows acquisition of a clearer tomography image P1.

Embodiment 2

Next, description will be given of tomography apparatus 20 according to Embodiment 2. The tomography apparatus 20 according to Embodiment 2 includes a positron emission tomography device (PET device) in addition to the apparatus configuration of Embodiment 1. Here, in the tomography apparatus 20 according to Embodiment 2, explanation is to be omitted to same elements as those in the apparatus configuration of Embodiment 1.

The tomography apparatus 20 includes a gantry 10a concerning a PET device 1a besides the gantry 10. The gantry 10a also has a through hole extending in the z-direction into which the top board 2 is inserted. Accordingly, the PET device 1a is provided adjacent to the X-ray tube 3 and the FPD 4 in the z-direction.

The gantry 10a includes inside thereof a detector ring 32 in a ring shape along a contour of the gantry 10a. The detector ring 32 has detector rings arranged in a ring shape that may detect gamma-rays.

A coincidence unit 33 is provided for performing coincidence to detection data outputted from the detector ring 32. Detection frequency and detection positions of annihilation gamma-rays pairs simultaneously entering into a portion in the detector ring 32 may be identified with the coincidence unit 33. The coincidence unit 33 outputs results of coincidence to a PET image generation section 34. The PET image generation section 34 calculates generating positions of annihilation gamma-ray pairs in accordance with the detection frequency and the detecting position identified with the coincidence unit 33, thereby generating a PET image P2 having mapped intensity in occurrence of annihilation gamma-ray pairs. The PET image P2 is a tomography image showing distribution of occurrence of annihilation-gamma-rays pairs.

The tomography apparatus 20 may acquire both of the tomography image P1 with X-rays and the PET image P2 with annihilation gamma-ray pairs through one inspection. For generation of both images P1 and P2 with use of the tomography apparatus 20, positron emission type radiopharmaceutical is firstly injected into the subject M. The radiopharmaceutical has a property of concentrating on a specific site portions, such as a lesion of the subject M. The radiopharmaceutical emits a positron. The positron generates an annihilation-gamma-rays pair that travels at a straight angle opposite to each other. Accordingly, an annihilation-gamma-rays pair is to be emitted from the subject M. Since distribution of radiopharmaceutical differs within the subject, the frequency of annihilation-gamma-rays pairs differs in sites of the subject M.

Figure 8:
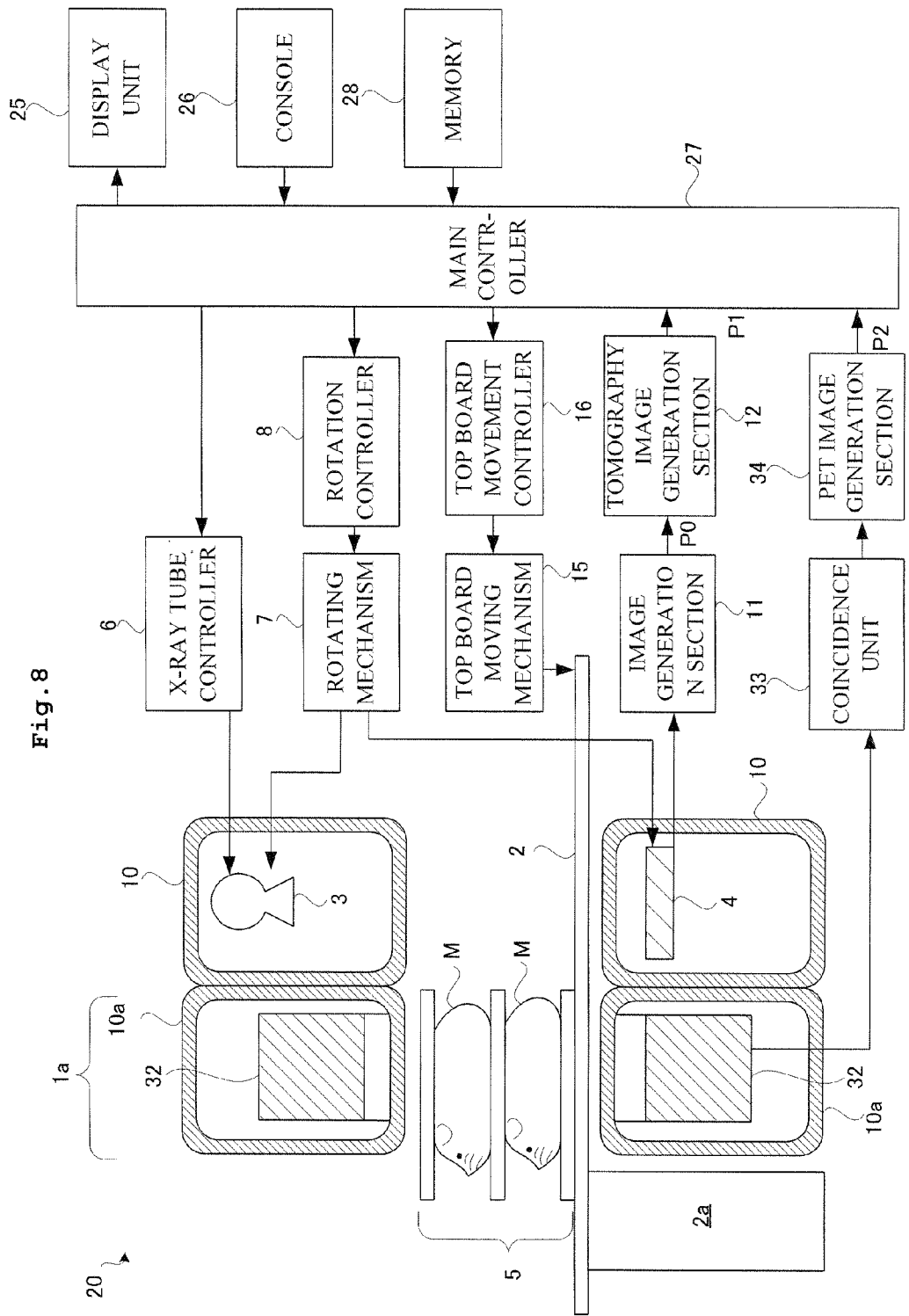
FIG. 8 is a functional block diagram illustrating a configuration of X-ray tomography apparatus according to Embodiment 2.

A sufficient time lapses from injection of radiopharmaceutical, and then the subject M is anesthetized and housed into the holder 5. That is, one anesthetized subject M is housed in every space 5a of the holder 5. Thereafter, the holder 5 having two or more subjects M housed therein is placed on the top board 2. When the experimenter provides instructions via the console 26 to the tomography apparatus 20 to start imaging of PET images, the top board 2 slides to guide the subject M into the through hole of the gantry 10a (see FIG. 8.) From this time, the detector ring 32 starts detection of an annihilation-gamma-rays pair, and the PET image generation section 34 generates a PET image P2. The frequency of annihilation-gamma-rays pairs is mapped in the PET image P2 that varies in sites of the subject M. Since distribution of the frequency of annihilation-gamma-rays pairs corresponds to distribution of radiopharmaceutical, the experimenter can recognize distribution of radiopharmaceutical in the subject through diagnosis of the PET image P2. When the field of view in the z-direction of the PET device 1a does not entirely cover the total body of the subject M in radiography, the PET image P2 may be imaged while the top board 2 slides in the z-direction.

Following operations are similar to the foregoing Step S2 and subsequent ones. The tomography image P1, the PET image P2, and a composite image having both the images superimposed are displayed on the display unit 25, and radiography is completed.

As mentioned above, the foregoing configuration is one specific aspect of Embodiment 1. With the positron emission type tomography apparatus, functional and structural images of the subject M may both be acquired, which results in more information acquired through imaging.

This invention is not limited to the foregoing configurations, but may be modified as follows:

(1) According to Embodiment 1, the space discriminating member 5c of the holder 5 has a shape of Arabic numerals. Alternatively, the shape may be alphabet, or other characters and graphic symbols.

(2) According to Embodiment 1, the space discriminating member 5c of the holder 5 has a shape of Arabic numerals. Alternatively, the space discriminating member 5c in the same cut shape may have various directions when it falls on the tomography image P1, thereby discriminating each subject M. Moreover, the space discriminating member 5c in the same cut shape may have a mirror-image symmetrical shape when it falls on the tomography image P1, thereby discriminating each subject M. Moreover, the space discriminating member 5c in the same cut shape may have various numbers, thereby discriminating each subject M. These aspects may realize discrimination of the cross section of the space discriminating member 5c. Accordingly, the sectional shape of the space discriminating member 5c in this invention is expediently to be included in the aspect that the space discriminating member 5c has a unique sectional shape.

Figure 9:
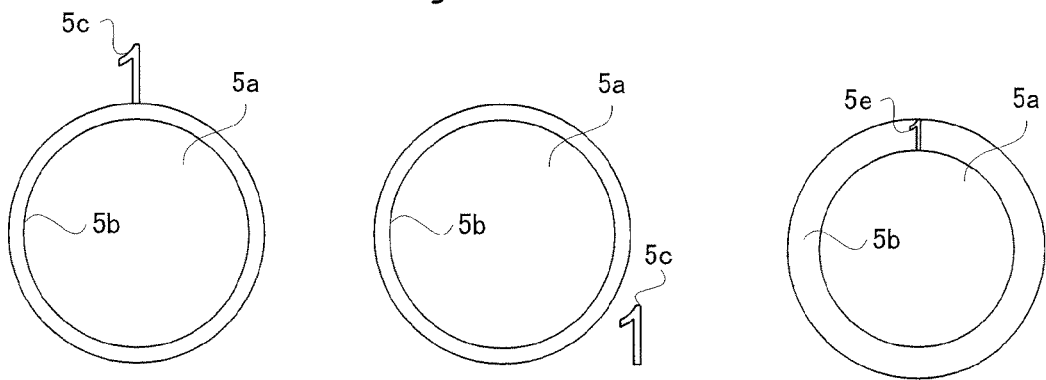
FIG. 9 is a plan view illustrating a configuration of one modification according to this invention.
Figure 10:
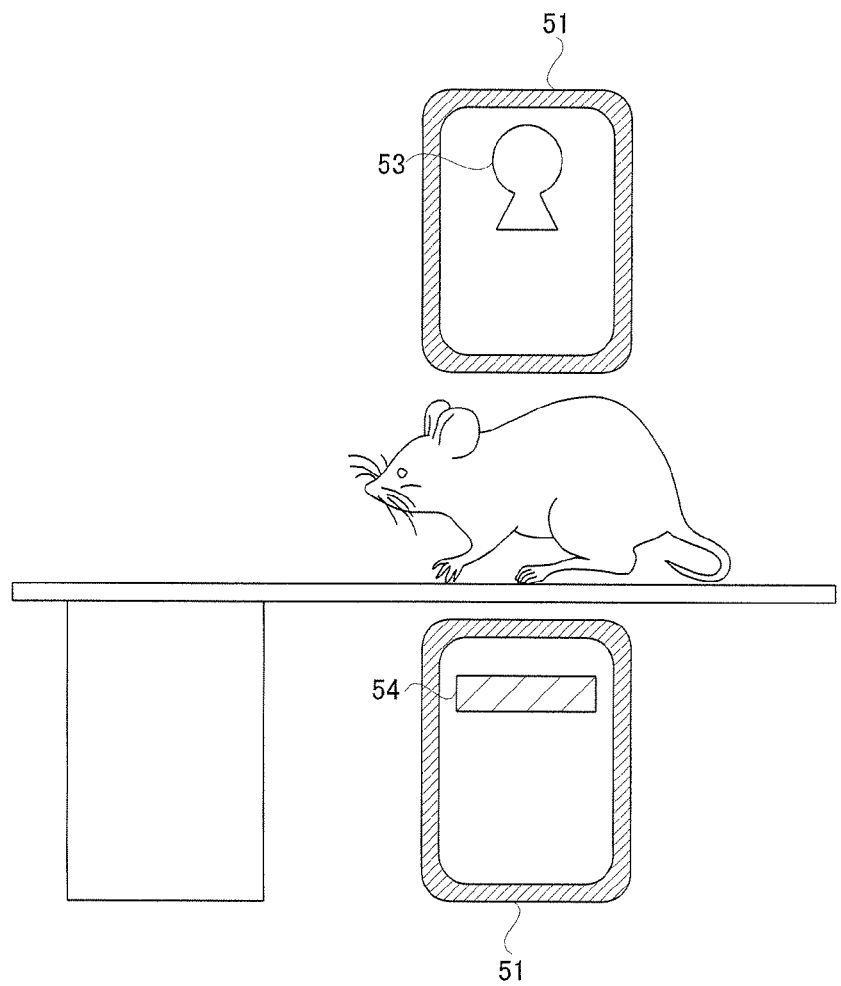
FIG. 10 is a schematic view illustrating a conventional configuration of radiographic apparatus.

(3) According to Embodiment 1, the space discriminating member 5c is provided inside of the space 5a. Alternatively, as shown on the left in FIG. 9, the space discriminating member 5c may be provided outside of the cylinder 5b. Moreover, as shown in the middle in FIG. 9, the space discriminating member 5c may be inserted into the cylinder 5b. Moreover, as shown on the right in FIG. 9, a long hole 5e is provided, instead of the space discriminating member 5c, in the cylinder 5b. When the long hold 5e is filled with a certain filler material and the cylinder 5b is cut along a plane where the imaginary circle VC exists, the filler material has a sectional shape that allows discrimination of the space 5a (i.e., the subject).

(4) According to Embodiment 1, the subject M is a mouse. Alternatively, another smaller animal may also be adopted as the subject M.

(5) According to Embodiment 1, the holder 5 has five spaces 5a. Alternatively, the number of spaces 5a may vary in accordance with a size of the smaller animals to be imaged.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. Radiation tomography apparatus comprising:
a radiation source for emitting radiation;
a radiation detecting device for detecting radiation;
an image generation device for generating fluoroscopic images from detection signals of the radiation detecting device;
a tomography image generation device for reconstructing a series of fluoroscopic images, thereby generating tomography images;
a rotary device for rotating the radiation source; and
a holder provided between the radiation source and the radiation detecting device that has two or more spaces for placing a subject,
the holder including space discriminating members extending continuously and absorbing radiation for each of the spaces, and
each of the space discriminating members extending toward a rotation axis of the radiation source and having a substantially columnar shape along the entire rotation axis of the radiation source, each space discriminating member being parallel to a corresponding space among the two or more spaces for placing subject, and each of the space discriminating members having a unique sectional shape when cut along a plane where an imaginary circle exists, the imaginary circle being a locus of rotation of the radiation source.

2. The radiation tomography apparatus according to claim 1, wherein
the space discriminating member is inserted inside of the space.

3. The radiation tomography apparatus according to claim 2, wherein
one subject is inserted into each of the spaces provided in the holder.

4. The radiation tomography apparatus according to claim 2, wherein
the space discriminating member is made from an acrylic resin.

5. The radiation tomography apparatus according to claim 2, further comprising:
a top board for supporting the holder; and
a top board moving device for moving the top board in a direction perpendicular to the imaginary circle.

6. The radiation tomography apparatus according to claim 2, further comprising:
positron emission type tomography apparatus adjacent to the radiation source and the radiation detecting device in a direction perpendicular to the imaginary circle.

7. The radiation tomography apparatus mouse according to claim 1, wherein
one subject is inserted into each of the spaces provided in the holder.

8. The radiation tomography apparatus according to claim 3, wherein
the space discriminating member is made from an acrylic resin.

9. The radiation tomography apparatus according to claim 7, further comprising:
a top board for supporting the holder; and
a top board moving device for moving the top board in a direction perpendicular to the imaginary circle.

10. The radiation tomography apparatus according to claim 7, further comprising:
positron emission type tomography apparatus adjacent to the radiation source and the radiation detecting device in a direction perpendicular to the imaginary circle.

11. The radiation tomography apparatus according to claim 1, wherein
the space discriminating member is made from an acrylic resin.

12. The radiation tomography apparatus according to claim 11, further comprising:
a top board for supporting the holder; and
a top board moving device for moving the top board in a direction perpendicular to the imaginary circle.

13. The radiation tomography apparatus according to claim 11, further comprising:
positron emission type tomography apparatus adjacent to the radiation source and the radiation detecting device in a direction perpendicular to the imaginary circle.

14. The radiation tomography apparatus according to claim 1, further comprising:
  a top board for supporting the holder; and
  a top board moving device for moving the top board in a direction perpendicular to the imaginary circle.

15. The radiation tomography apparatus according to claim 14, further comprising:
  positron emission type tomography apparatus adjacent to the radiation source and the radiation detecting device in a direction perpendicular to the imaginary circle.

16. The radiation tomography apparatus according to claim 1, further comprising:
  positron emission type tomography apparatus adjacent to the radiation source and the radiation detecting device in a direction perpendicular to the imaginary circle.

* * * * *